United States Patent
Simandan et al.

(10) Patent No.: US 9,206,203 B2
(45) Date of Patent: Dec. 8, 2015

(54) CATALYTIC PROCESS FOR THE PREPARATION OF THIOCARBOXYLATE SILANE

(71) Applicant: Momentive Performance Materials Inc., Waterford, NY (US)

(72) Inventors: Tiberiu Ladislau Simandan, Termoli (IT); Ilaria Vecchi, Casalbordino (IT); Holger Jurgen Glatzer, Leverkusen (DE)

(73) Assignee: Momentive Performance Materials Inc., Waterford, NY (US)

( * ) Notice: Subject to any disclaimer, the term of this patent is extended or adjusted under 35 U.S.C. 154(b) by 42 days.

(21) Appl. No.: 14/226,345

(22) Filed: Mar. 26, 2014

(65) Prior Publication Data

US 2014/0296553 A1  Oct. 2, 2014

Related U.S. Application Data

(60) Provisional application No. 61/806,489, filed on Mar. 29, 2013.

(51) Int. Cl.
| | |
|---|---|
| C07F 7/04 | (2006.01) |
| C07F 7/08 | (2006.01) |
| C07C 51/41 | (2006.01) |
| C07C 327/06 | (2006.01) |
| C07F 7/18 | (2006.01) |
| C07C 327/16 | (2006.01) |
| B01J 31/02 | (2006.01) |

(52) U.S. Cl.
CPC .............. *C07F 7/0818* (2013.01); *C07C 51/41* (2013.01); *C07C 327/06* (2013.01); *C07C 327/16* (2013.01); *C07F 7/1836* (2013.01); *C07F 7/1892* (2013.01); *B01J 31/0239* (2013.01); *B01J 31/0254* (2013.01)

(58) Field of Classification Search
CPC ............................. C07F 7/0818; C07C 51/41
USPC ....................................................... 556/428
See application file for complete search history.

(56) References Cited

U.S. PATENT DOCUMENTS

| | | | |
|---|---|---|---|
| 6,528,673 B2 | 3/2003 | Cruse et al. | |
| 7,528,273 B2 | 5/2009 | Simandan et al. | |
| 7,781,606 B2 | 8/2010 | Cruse et al. | |
| 8,008,520 B2 | 8/2011 | Cruse et al. | |
| 8,008,524 B2 | 8/2011 | Cruse et al. | |
| 8,097,743 B2 | 1/2012 | Glatzer et al. | |
| 2003/0130388 A1 | 7/2003 | Luginsland et al. | |
| 2005/0245753 A1 | 11/2005 | Cruse et al. | |
| 2005/0277781 A1 | 12/2005 | Cruse et al. | |
| 2006/0235236 A1* | 10/2006 | Simandan ............. | C07F 7/1892 556/429 |

OTHER PUBLICATIONS

Hilal et al., Journal of Molecular Catalysis A: Chemical 144 (1999) 47-59.*
Gupta et al., Coordination Chemistry Reviews 253 (2009) 1926-1946.*
Tomoi M. Ed-Y. Sasson et al., "Transfer Catalysis", (Jan. 1, 1997), Hanbook of Phase Transfer Catalysis, Springer NL, pp. 424-461, XP008170352.
Glatzer, et al., "Triphase catalysis: a new rotating disk contactor for measuring mass transfer coefficients", Chemical Engineering Science, vol. 53, No. 13, pp. 2431-2449.
Glatzer, et al. "Rate enhancements due to autocatalysis and heterogenization in phase transfer catalysis: a comparative study", Chemical Engineering Science, 55 (2000) pp. 5149-5160.
Satrio, et al. "Triphase catalysis: a rigorous mechanistic model for nucleophilic substitution reactions based on a modified Langmuir-Hinshelwood/Eley-Rideal approach", Chemical Engineering Science, 55 (2000) pp. 5013-5033.
Glatzer, et al., "Triphase catalysis: a correlation for Sherwood number using the rotating disk contactor (RDC) developed earlier", Chemical Engineering Science, 56 (2001) pp. 3815-3827.
Desikan, Spidhar; Doraiswamy, L.K. (2000) "Enhanced activity of polymer-supported phase transfer catalysts", Chemical Engineering Science, 55 (24), pp. 6119-6127.
International Search Report and Written Opinion of the International Searching Authority dated Jul. 17, 2014.

* cited by examiner

*Primary Examiner* — Porfirio Nazario Gonzalez
*Assistant Examiner* — Kofi Adzamli
(74) *Attorney, Agent, or Firm* — James C. Abruzzo

(57) ABSTRACT

The invention is directed to a process for the preparation of thiocarboxylate silane comprising reacting an aqueous solution of a salt of a thiocarboxylic acid with a haloalkyl silane in the presence of a solid inorganic oxide-supported phase transfer catalyst. The invention is also directed to a process for the preparation of an aqueous solution of a salt of a thiocarboxylic acid which comprises reacting an aqueous solution of a sulfide and/or hydrosulfide with an acid halide in the presence of a said solid catalyst.

23 Claims, No Drawings

CATALYTIC PROCESS FOR THE PREPARATION OF THIOCARBOXYLATE SILANE

This application claims priority to Provisional U.S. Patent Application No. 61/806,489, filed Mar. 29, 2013, the entire contents of which are incorporated herein by reference in its entirety.

FIELD OF THE INVENTION

The present invention relates to a polymer-supported phase transfer catalyst for use in the process of making thiocarboxylate silane. More specifically, the present invention relates to a solid inorganic oxide-supported quaternary ammonium halide phase transfer catalyst, in which the quaternary ammonium halide is covalently bonded to the inorganic oxide, such as silica-supported tributylpropyl ammonium halide phase transfer catalyst, and its use in producing thiocarboxylate-containing hydrolysable silanes, such as 3-octanoylthio-1-propyltriethoxy silane.

BACKGROUND OF THE INVENTION

Thiocarboxylate-containing hydrolysable silanes are sulfur silane coupling agents which are used extensively in rubber applications such as tires and tire components. Unfortunately, the catalysts that are used in the process of making such thiocarboxylate-containing hydrolysable silanes tend to be difficult to separate from the reaction mixture, and can at times contaminate the product or the aqueous phase containing the mixture and/or product. In addition, there still exists a need for a catalyst that can be used in the processes of making thiocarboxylate-containing hydrolysable silanes but with improved catalytic activity.

SUMMARY OF THE INVENTION

The invention is directed to expeditious production of a thiocarboxylate-containing hydrolysable silane coupling agent by employing a solid inorganic oxide-supported phase transfer catalyst which is a solid inorganic oxide-supported phase transfer catalyst comprising quaternary ammonium halide group(s) in which the quaternary ammonium halide is covalently bonded to the inorganic oxide, such as solid silica-supported tributyl propyl ammonium halide phase transfer catalyst, which allows for the catalyst to be easily removed and/or recycled in the process while still providing beneficial catalytic activity.

In one embodiment herein there is provided a process for the preparation of thiocarboxylate silane comprising reacting an aqueous solution of a salt of a thiocarboxylic acid with a haloalkyl silane in the presence of a solid inorganic oxide-supported quaternary ammonium halide phase transfer catalyst of the formula (I):

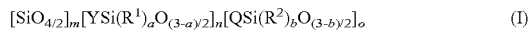

$$[SiO_{4/2}]_m[YSi(R^1)_aO_{(3-a)/2}]_n[QSi(R^2)_bO_{(3-b)/2}]_o \qquad (I)$$

wherein:
each occurrence of Y is independently a quaternary ammonium halide-containing group having the structure of the formula (II):

$$[X^-][R^3R^4R^5N^+R^6-] \qquad (II)$$

wherein each $R^3$, $R^4$ and $R^5$ is independently an alkyl containing from 1 to 12 carbon atoms, more specifically 2 to 6 carbon atoms, and even more specifically 4 carbon atoms, phenyl or benzyl; each $R^6$ is an alkylene group containing from 1 to 6 carbon atoms, more specifically 1 to 3 carbon atoms and even more specifically 3 carbon atoms;
and $X^-$ is a halide selected from the group consisting of $F^-$, $Cl^-$, $Br^-$ and $I^-$, more specifically $Cl^-$ or $Br^-$, and more specifically $Br^-$;

each occurrence of Q is independently an organic group selected from the group consisting of a hydrocarbon group having from 1 to 18 carbon atoms, more specifically from 3 to 15 carbon atoms and even more specifically from 4 to 12 carbon atoms, and a heterocarbon group containing from 1 to 18 carbon atoms and at least one heteroatom selected from the group consisting of oxygen, sulfur and nitrogen, with the proviso that the heterocarbon group is bonded to the silicon atom through a C—Si bond;

each occurrence of $R^1$ and $R^2$ is independently selected from the group consisting of an alkyl group of from 1 to 6 carbon atoms, more specifically 1 carbon atom and phenyl;

each occurrences of the subscripts a, b, m, n and o is independently an integer, wherein a is from 0 to 2, more specially 0 or 1, and even more specifically 0; b is from 0 to 2, more specially 0 or 1, and even more specifically 0; m is a positive integer, n is a positive integer and o is 0 or a positive integer, with the provisos that the molar ratio of m:n is from 5:1 to 225:1, more specifically from 20:1 to 150:1, and even more specifically, from 25:1 to 75:1; and the molar ratio of o:n is from 0:1 to 3:1, more specifically from 0:1 to 0:2 and even more specifically 0:1, to provide for the thiocarboxylate-containing hydrolysable silane.

The values of the subscripts m and n are chosen so that the weight percent of the $[YSi(R^1)_aO_{(3-a)/2}]$ repeat unit is from 1 to 50 weight percent, more specifically from 3 to 20 weight percent, and even more specifically from 5 to 17 weight percent, based upon the weight of the total solid support, $[SiO_{4/2}]_m[YSi(R^1)_aO_{(3-b)/2}]_o$.

There is also provided herein a process for the preparation of an aqueous solution of a salt of a thiocarboxylic acid which comprises reacting an aqueous solution of a sulfide and/or hydrosulfide with an acid halide and/or acid anhydride in the presence of a solid inorganic oxide-supported quaternary ammonium halide phase transfer catalyst of the above-noted general formula to provide the aqueous solution of thiocarboxylic acid salt.

DETAILED DESCRIPTION OF THE INVENTION

Catalyst (Phase Transfer Catalyst)

Specific examples of suitable phase transfer catalysts for use in the process for making a thiocarboxylate-containing hydrolysable silane or an aqueous solution of an alkali or ammonium salt of a thiocarboxylic acid herein are solid inorganic oxide-supported quaternary ammonium halide phase transfer catalyst, where the solid oxide is a metal oxide or a metalloid oxide and wherein the solid inorganic oxide-supported quaternary ammonium halide phase transfer catalyst comprises chemically bonded quaternary ammonium halide groups having the structure of the structure of formula (III):

$$[YSi(R^1)_aO_{(3-a)/2}] \qquad (III)$$

wherein
each occurrence of Y is independently a quaternary ammonium halide-containing group having the structure of the formula (II):

$$[X^-][R^3R^4R^5N^+R^6-] \qquad (II)$$

wherein each occurrence of $R^1$ is independently selected from the group consisting of an alkyl group of from 1 to 6 carbon atoms, or an aryl group of from 6 to 8 carbon atoms, more specifically an alkyl of from 1 to 3 carbon atoms, even more specifically an alkyl of 1 carbon atom and phenyl; each $R^3$, $R^4$ and $R^5$ is independently an alkyl containing from 1 to 12 carbon atoms or an aryl of from 6 to 8 carbon atoms, more specifically an alkyl containing from 2 to 6 carbon atoms, and even more specifically an alkyl of 4 carbon atoms, phenyl or benzyl; each $R^6$ is an alkylene group containing from 1 to 6 carbon atoms, more specifically an alkylene of 1 to 3 carbon atoms and even more specifically an alkylene of 3 carbon atoms;

and $X^-$ is a halide selected from the group consisting of $F^-$, $Cl^-$, $Br^-$ and $I^-$, more specifically $Cl^-$ or $Br^-$, and more specifically $Br^-$, and a is an integer 0, 1 or 2, and wherein the weight percent of the $[YSi(R^1)_aO_{(3-a)/2}]$ group is from 1 to 50 weight percent, more specifically from 3 to 20 weight percent, and even more specifically from 5 to 17 weight percent, based upon the weight of the total solid support; and optionally, wherein the solid inorganic oxide-supported quaternary ammonium halide phase transfer catalyst further comprises an organic group having the structure of formula (IV):

$$[QSi(R^2)_bO_{(3-b)/2}] \quad (IV)$$

wherein each occurrence of $R^2$ is independently selected from the group consisting of an alkyl group of from 1 to 6 carbon atoms, or an aryl group of from 6 to 8 carbon atoms, more specifically from an alkyl of from 1 to 3 carbon atoms, even more specifically an alkyl of 1 carbon atom and phenyl; each occurrence of Q is independently an organic group selected from the group consisting of a hydrocarbon group having from 1 to 18 carbon atoms, more specifically from 3 to 15 carbon atoms and even more specifically from 4 to 12 carbon atoms, and a heterocarbon group containing from 1 to 18 carbon atoms and at least one heteroatom selected from the group consisting of oxygen, sulfur and nitrogen, with the proviso that the heterocarbon group is bonded to the silicon atom through a C—Si bond, and the subscript b is an integer 0, 1 or 2, more specifically 1 or 2 and even more specifically 1, wherein the weight percent of the $[QSi(R^2)_bO_{(3-b)/2}]$ is from 0 to 20 weight percent, more specifically 0 to 10 weight percent and even more specially, 0 weight percent, where the weight percents are based upon the total weight of the solid inorganic oxide-supported quaternary ammonium halide phase transfer catalyst.

In one embodiment, the inorganic oxide used as a support is a metal oxide or metalloid oxide, or mixtures of metal oxide and metalloid oxide. Representative examples of metal oxide are alumina oxide, iron (II) and (III) oxides, copper (II) oxide, and titanium oxide. Metalloid oxides include silicate, such as silica. The inorganic oxide support and be mixtures of metal oxide or mixtures of metal oxides and metalloid oxides, such as for example clays, borosilicate glasses, and mica.

The quaternary ammonium groups, $[YSi(R^1)_aO_{(3-a)/2}]$, and if present, the organic groups, $[QSi(R^2)_bO_{(3-b)/2}]$, are bonded to the surface of the inorganic oxide, or these group are present on the surface of the inorganic oxide, in pore of the inorganic oxide, and in the interior of the inorganic oxide solid support.

In one embodiment herein there is provided a process for the preparation of thiocarboxylate silane comprising reacting an aqueous solution of a salt of a thiocarboxylic acid with a haloalkyl silane in the presence of solid inorganic oxide-supported quaternary ammonium halide phase transfer catalyst of the formula (I):

$$[SiO_{4/2}]_m[YSi(R^1)_aO_{(3-a)/2}]_n[QSi(R^2)_bO_{(3-b)/2}]_o \quad (I)$$

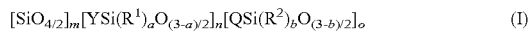

wherein:

each occurrence of Y is independently a quaternary ammonium halide-containing group having the structure of the formula (II):

$$[X^-][R^3R^4R^5N^+R^6\text{—}] \quad (II)$$

wherein each $R^3$, $R^4$ and $R^5$ is independently an alkyl containing from 1 to 12 carbon atoms, more specifically an alkyl of from 2 to 6 carbon atoms, and even more specifically an alkyl of 4 carbon atoms, phenyl or benzyl; each $R^6$ is an alkylene group containing from 1 to 6 carbon atoms, more specifically an alkylene group of from 1 to 3 carbon atoms and even more specifically an alkylene group of 3 carbon atoms;

and $X^-$ is a halide selected from the group consisting of $F^-$, $Cl^-$, $Br^-$ and $I^-$, more specifically $Cl^-$ or $Br^-$, and more specifically $Br^-$;

each occurrence of Q is independently an organic group selected from the group consisting of a hydrocarbon group having from 1 to 18 carbon atoms, more specifically from 3 to 15 carbon atoms and even more specifically from 4 to 12 carbon atoms, and a heterocarbon group containing from 1 to 18 carbon atoms and at least one heteroatom selected from the group consisting of oxygen, sulfur and nitrogen, with the proviso that the heterocarbon group is bonded to the silicon atom through a C—Si bond;

each occurrence of $R^1$ and $R^2$ is independently selected from the group consisting of an alkyl group of from 1 to 6 carbon atoms, or an aryl group of from 6 to 8 carbon atoms, more specifically an alkyl of from 1 to 3 carbon atoms, even more specifically an alkyl of 1 carbon atom and phenyl;

each occurrences of the subscripts a, b, m, n and o is independently an integer, wherein a is from 0 to 2, more specially 0 or 1, and even more specifically 0; b is from 0 to 2, more specially 0 or 1, and even more specifically 0; m is a positive integer, n is a positive integer and o is 0 or a positive integers, with the provisos that the molar ratio of m:n is from 5:1 to 225:1, more specifically from 20:1 to 150:1, and even more specifically, from 25:1 to 75:1; and the molar ratio of o:n is from 0:1 to 3:1, more specifically from 0:1 to 0:2 and even more specifically 0:1, to provide for the thiocarboxylate-containing hydrolysable silane.

In another embodiment, the values of the subscripts m and n are chosen so that the weight percent of the $[YSi(R^1)_aO_{(3-a)/2}]$ repeat unit is from 1 to 50 weight percent, more specifically from 3 to 20 weight percent, and even more specifically from 5 to 17 weight percent, based upon the weight of the total solid support, $[SiO_{4/2}]_m[YSi(R^1)_aO_{(3-a)/2}]_n[QSi(R^2)_bO_{(3-b)/2}]_o$.

In yet another embodiment, $R^3$, $R^4$ and $R^5$ are butyl, $R^6$ is propylene, $X^-$ is chloride or bromide, Q is 5-hydroxy-3-thiapentyl, 6-hydroxy-4-thia-hexyl, 3-thiapentadecyl, 4-thiahexadecyl, methyl, ethyl, hexyl, heptyl, octyl, decyl or dodecyl, more specifically, 6-hydroxy-4-thia-hexyl, 4-thiahexadecyl, and the molar ratio of n:o is from 0:1 to 1:1.

In yet still another embodiment, $R^3$, $R^4$ and $R^5$ are butyl, $R^6$ is propylene, $X^-$ is chloride or bromide and o is equal to 0, and the ratio of m:n 20:1 to 150:1.

The solid inorganic supported-quaternary ammonium halide phase transfer catalyst employed in the process can be represented by the figure:

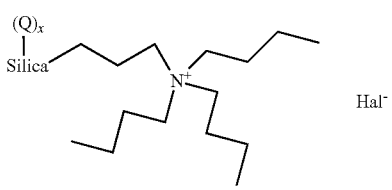

wherein Hal- is a halogen atom, such as Cl⁻, Br⁻, I⁻ and F⁻, Q is a hydrocarbon substituent (e.g., either a hydrophobic or hydrophilic chain) of from 1 to about 18 carbon atoms, specifically from 3 to about 15 carbon atoms, more specifically from 4 to about 12 carbon atoms, which is optionally heteroatom substituted with at least one S, O, or N atom, and x is the molar ratio of the Q groups to the quaternary ammonium group, which is from 0 to 3. It is understood that the figure represents a single quaternary ammonium halide group or cases which have more than one quaternary ammonium halide group on the solid support. In one embodiment x is zero and there are no hydrophilic or hydrophobic Q groups.

The solid inorganic oxide supported-quaternary ammonium halide phase transfer catalyst are in the form of particles, sphere, sheet-like structures, fibrous shapes, and irregular shapes, more specifically particles or spheres.

In one embodiment, the solid inorganic oxide supported quaternary ammonium halide phase transfer catalyst is a solid particle with particle size of from 0.5 to 2,000 micrometers (µm), more specifically between 100 and 1,000 micrometers, and even more specially, between 200 and 500 micrometers, as measured in accordance with ASTM B822-10 method, Standard Test Method for Particle Size Distribution of Metal Powders and Related Compounds by Light Scattering.

It will be understood herein that any ranges and subranges described herein can further comprise any combination of any endpoints of said ranges and/or subranges.

In one embodiment herein the catalyst is selected from the group consisting of chloride, tributylammonium propyl, silica; chloride, tributylammonium propyl, 2-hydroxyethyl sulfide ethyl silica; chloride, tributylammonium propyl, dodecyl sulfide ethyl silica; bromide, tributylammonium propyl, silica; combinations thereof and aqueous solutions thereof.

The solid inorganic supported-quaternary ammonium halide phase transfer catalyst herein also referred to as phase transfer catalyst or catalyst, can be added to the reaction medium as salts, or as concentrated or dilute solutions in water and/or other suitable solvents, such as alcohols.

The quantity of solid inorganic oxide supported-quaternary ammonium halide phase transfer catalyst used will depend on the desired rate of reaction and the level of side products which can be tolerated, among other factors. Suitable concentrations include a concentration of equal to or greater than 1 part per million based on the total weight of the reaction mixture, more specifically from about 1 ppm (part per million by weight) to about 15 percent by weight based on the total weight of the reaction medium, even more specifically, from about 10 ppm to about 1 weight percent and advantageously from about 50 ppm to about 0.5 weight percent based on the total weight of the reaction medium. Quantities below 1 ppm of phase transfer catalyst might be much the same as those obtained without the use of a phase transfer catalyst.

In one embodiment herein the solid inorganic oxide-supported quaternary ammonium halide phase transfer catalyst is present in an amount such that the weight percent amount of the $YSi(R^1)_aO_{(3-a)/2}$, where Y is propyl tributyl ammonium halide functionality based on the total weight of the catalyst is from about 3 weight percent to about 20 weight percent, more specifically from about 4 weight percent to about 18 weight percent and most specifically from about 5 weight percent to about 17 weight percent. In one embodiment there is more than one propyl tributyl ammonium functionality per silica component, more specifically from about 2 to about 5 functionalities, and most specifically from about 2 to about 3 functionalities.

In one further embodiment, the average particle size of the solid silica supported-quaternary ammonium halide phase transfer catalyst employed herein is from about 50 to about 600 micrometers, more specifically from about 100 to about 550 micrometers and most specifically from about 60 to about 500 micrometers, as measured in accordance with ASTM B822-10, Standard Test Method for Particle Size Distribution of Metal Powders and Related Compounds by Light Scattering. Alternatively stated the catalyst has a pore size of from about 35 to about 220 angstroms, more specifically from about 40 to about 210 angstroms and most specifically from about 45 to about 200 angstroms. In one embodiment, the pore size is from 80 to about 110 angstroms.

Silane Structures

In accordance with the present invention as hereinafter more fully described and claimed, there is provided a process for the preparation of thiocarboxylate silane which comprises reacting an aqueous solution of thiocarboxylic acid salt with a haloalkyl silane in the presence of a catalytically effective amount of phase transfer catalyst to provide thiocarboxylate silane.

The invention herein provides a simple and efficient process of the manufacture of thiocarboxylate silane. The process requires no solvent other than water, uses existing aqueous sulfide raw materials as the sulfur source and requires no hazardous alkali metals or hydrogen sulfide as feedstock.

The thiocarboxylate silanes, whose preparation by an aqueous route is described herein, may be represented by Formulae (V), (VI), (VII) and (VIII):

$$R^7C(=O)-S-G^2(-SiX'_3)_f \quad (V);$$

$$G^1[-C(=O)-S-G^2(-SiX'_3)_f]_e \quad (VI);$$

$$[G^1(-Y-S-)_e]_g[G^2(-SiX'_3)_f]_d \quad (VII); \text{ and,}$$

$$X_3SiGSC(=O)GC(=O)SGSiX'_3 \quad (VIII)$$

wherein each occurrence of $R^7$ is independently selected form the group consisting of hydrogen, alkyl, cycloalkyl, alkenyl, alkynyl, aryl and aralkyl groups, with each $R^7$ other than hydrogen containing from 1 to 30 carbon atoms; each G is a divalent alkylene having from 1 to 10 carbon atoms or phenylene, each separate occurrence of $G^1$ and $G^2$ is independently a polyvalent group (divalent or higher valency) derived by substitution of an alkyl, cycloalkyl, alkenyl, aryl or aralkyl group, wherein $G^1$ and $G^2$ can contain from 1 to 30 carbon atoms; each occurrence of X' is independently a member selected from the group consisting of $R^8O-$, $R^8_2C=NO-$, $R^8_2NO-$ or $R^8_2N-$, $-R^8$, and $-(OSiR^8_2)_t(OSiR^8_3)$, wherein each $R^8$ is independently selected form the group consisting of hydrogen, alkyl, cycloalkyl, alkenyl, alkynyl, aryl and aralkyl groups, with each $R^8$ other than hydrogen containing from 1 to 30 carbon atoms and at least one X' is not $-R^8$ and each occurrence of the subscript t is 0 or an integer of from 1 to about 50; each occurrence of the subscript d is independently an integer from 1 to 100; each occurrence of the subscript e is independently an integer from 2 to 6; each occurrence of the subscript f is independently an integer from 1 to 6; and, each occurrence of the subscript g is independently an integer from 1 to 100.

As used herein, alkyl includes straight chain alkyl or branched alkyl group; alkenyl includes any straight chain alkenyl or branched alkenyl group containing one or more carbon-carbon double bonds, where the point of substitution can be either at a carbon-carbon double bond or elsewhere in the group; and alkynyl includes any straight chain alkynyl or branched alkynyl group containing one or more carbon-carbon triple bonds and optionally also one or more carbon-carbon double bonds as well, where the point of substitution can be either at a carbon-carbon triple bond, a carbon-carbon double bond, or elsewhere in the group. Specific examples of alkyls include methyl, ethyl, propyl and isobutyl. Specific examples of alkenyls include vinyl, propenyl, allyl and methallyl. Specific examples of alkynyls include acetylenyl, propargyl and methylacetylenyl.

As used herein, aryl includes any aromatic hydrocarbon from which one hydrogen atom has been removed; aralkyl includes any of the aforementioned alkyl groups in which one or more hydrogen atoms have been substituted by the same number of like and/or different aryl (as defined herein) substituents; and arenyl includes any of the aforementioned aryl groups in which one or more hydrogen atoms have been substituted by the same number of like and/or different alkyl (as defined herein) substituents. Specific examples of aryls include phenyl and naphthalenyl. Specific examples of aralkyls include benzyl and phenethyl. Specific examples of arenyls include tolyl and xylyl.

As used herein, cycloalkyl, cycloalkenyl, and cycloalkynyl also include bicyclic, tricyclic, and higher cyclic structures as well as the aforementioned cyclic structures further substituted with alkyl, alkenyl, and/or alkynyl groups. Representative examples include norbornyl, norbornenyl, ethylnorbornyl, ethylnorbornenyl, ethylcyclohexyl, ethylcyclohexenyl, cyclohexylcyclohexyl and cyclododecatrienyl.

The key functional group present in the silanes of the present invention is the thiocarboxylate ester group, —C(=O)S— (any silane with this functional group is a "thiocarboxylate ester silane").

Examples of structures containing the group wherein $R^7C(=O)$— include those wherein $R^7$ has a primary carbon attached to the carbonyl and is advantageously a $C_2$-$C_{20}$ straight- or branched-chain alkyl, more particularly a $C_6$-$C_{18}$ straight-chain alkyl. Especially advantageous herein are $C_6$-$C_{14}$ straight-chain alkyls.

Representative examples of $G^1$ and $G^2$ include phenylene; —$(CH_2)_n$— wherein n is 1 to 20, such as —$CH_2$—, —$CH_2CH_2$—, —$CH_2CH_2CH_2$—, —$CH_2CH_2CH_2CH_2$—, and —$CH_2CH_2CH_2CH_2CH_2CH_2CH_2CH_2$—; branched chain alkyl groups, such as —$CH_2(CH_2)_mCH(CH_3)$— where m is zero to 17, —$CH_2CH_2CH(CH_3)$—, —$CH_2CH(CH_2CH_3)$—, —$CH_2CH_2CH_2CH(CH_3)$—, —$CH_2CH_2CH(CH_2CH_3)$—, —$CH_2CH(CH_3)CH_2CH_2$—, —$CH_2CH(CH_3)CH(CH_3)$—, —$CH_2C(CH_3)(CH_2CH_3)$—, —$CH_2CH_2CH(CH_3)CH_2$—, —$CH_2CH_2C(CH_3)_2$— and —$CH_2CH[CH(CH_3)_2]$—, —$CH_2CH(CH_2CH_2CH_3)$—, —$CH_2CH_2C(CH_3)_2CH_2$— and —$CH_2CH(CH_3)CH_2$—; any of the structures having a phenylene group, such as —$CH_2CH_2(C_6H_4)CH_2CH_2$—, —$CH_2CH_2(C_6H_4)CH(CH_3)$—, —$CH_2CH(CH_3)(C_6H_4)CH(CH_3)CH_2$— where the notation $C_6H_4$ denotes a disubstituted benzene ring; any structures containing a cyclohexyl ring, such as —$CH_2CH_2$-cyclohexyl-trisubstituted cyclohexane ring, —$CH_2CH_2(vinylC_6H_9)CH_2CH_2$—, and —$CH_2CH_2(vinylC_6H_9)CH(CH_3)$— where the notation $C_6H_9$ denotes any isomer of the trisubstituted cyclohexane ring.

Some specific structures for $G^1$ and $G^2$ are —$CH_2$—, —$CH_2CH_2$—, —$CH_2CH_2CH_2$— and —$CH_2CH(CH_3)CH_2$—. The structure —$CH_2CH_2CH_2$— is particularly advantageous.

Representative examples of $R^8$ groups include methyl, ethyl, propyl, isopropyl and butyl, phenyl, benzyl, tolyl, and, allyl. Some specific $R^8$ groups are $C_1$ to $C_4$ alkyls and H.

Representative examples of X' are methoxy, ethoxy, isobutoxy, propoxy, isopropoxy and oximato. Methoxy and ethoxy are particularly advantageous.

Included among the embodiments herein are those in which X' is $R^8O$— and $R^8$ is any of hydrogen, methyl, ethyl, propyl, butyl or isopropyl; and, $G^1$ or $G^2$ is a substituted phenyl or substituted $C_2$ to $C_{20}$ straight-chain alkyl.

Specific embodiments include those wherein p is zero, X is ethoxy and $R^7$ is a $C_6$-$C_{14}$ straight-chain alkyl.

Representative examples of the silanes whose preparation is described in the present invention include 2-triethoxysilyl-1-ethyl thioacetate; 2-trimethoxy-silyl-1-ethyl thioacetate; 2-(methyldimethoxysilyl)-1-ethyl thioacetate; 3-trimethoxy-silyl-1-propyl thioacetate; triethoxysilylmethyl thioacetate; trimethoxysilylmethyl thioacetate; triisopropoxysilylmethyl thioacetate; methyldiethoxysilylmethyl thioacetate; methyldimethoxysilylmethyl thioacetate; methyldiisopropoxysilylmethyl thioacetate; dimethylethoxysilylmethyl thioacetate; dimethylmethoxysilylmethyl thioacetate; dimethylisopropoxysilylmethyl thioacetate; 2-triisopropoxysilyl-1-ethyl thioacetate; 2-(methyldiethoxysilyl)-1-ethyl thioacetate; 2-(methyldiisopropoxysilyl)-1-ethyl thioacetate; 2-(dimethylethoxysilyl)-1-ethyl thioacetate; 2-(dimethylmethoxy-silyl)-1-ethyl thioacetate; 2-(dimethylisopropoxysilyl)-1-ethyl thioacetate; 3-triethoxysilyl-1-propyl thioacetate; 3-triisopropoxysilyl-1-propyl thioacetate; 3-methyldiethoxysilyl-1-propyl thioacetate; 3-methyldimethoxysilyl-1-propyl thioacetate; 3-methyldiisopropoxysilyl-1-propyl thioacetate; 1-(2-triethoxysilyl-1-ethyl)-4-thioacetylcyclohexane; 1-(2-triethoxysilyl-1-ethyl)-3-thioacetylcyclohexane; 2-triethoxysilyl-5-thioacetylnorbornene; 2-triethoxysilyl-4-thioacetylnorbornene; 2-(2-triethoxysilyl-1-ethyl)-5-thioacetylnorbornene; 2-(2-triethoxysilyl-1-ethyl)-4-thioacetylnorbornene; 6-triethoxysilyl-1-hexyl thioacetate; 1-triethoxysilyl-5-hexyl thioacetate; 8-triethoxysilyl-1-octyl thioacetate; 1-triethoxysilyl-7-octyl thioacetate; 6-triethoxysilyl-1-hexyl thioacetate; 1-triethoxysilyl-5-octyl thioacetate; 8-trimethoxysilyl-1-octyl thioacetate; 1-trimethoxysilyl-7-octyl thioacetate; 10-triethoxysilyl-1-decyl thioacetate; 1-triethoxysilyl-9-decyl thioacetate; 1-triethoxysilyl-2-butyl thioacetate; 1-triethoxy-silyl-3-butyl thioacetate; 1-triethoxysilyl-3-methyl-2-butyl thioacetate; 1-triethoxysilyl-3-methyl-3-butyl thioacetate; 3-trimethoxysilyl-1-propyl thiooctanoate; 3-triethoxysilyl-1-propyl thiopalmitate; 3-triethoxysilyl-1-propyl thiooctanoate, also known as 3-octanoylthio-1-propyltriethoxy silane, 3-triethoxysilyl-1-propyl thioloctoate and 3-triethoxysilyl-1-propyl thiocaprylate; 3-triethoxysilyl-1-propyl thiodecanoate; 3-triethoxysilyl-1-propyl thiododecanoate, also known as 3-triethoxysilyl-1-propyl thiolaurate; 3-triethoxysilyl-1-propyl thiotetradecanoate, also known as 3-triethoxysilyl-1-propyl thiomyristate; 3-triethoxysilyl-1-propyl thiobenzoate; 3-triethoxysilyl-1-propyl thio-2-ethylhexanoate; 3-triethoxysilyl-1-propyl thio-2-methyl heptanoate; bis-(3-triethoxysilyl-1-propyl)dithiophthalate; bis-(3-triethoxysilyl-1-propyl)dithio-iso-phthalate; bis-(3-triethoxysilyl-1-propyl)dithiotere-phthalate; bis-(3-triethoxysilyl-1-propyl) dithiosuccinate; bis-(3-triethoxysilyl-1-propyl) dithiooxalate; bis-(3-triethoxysilyl-1-propyl)dithiosebacate; and, bis-(3-triethoxysilyl-1-propyl)dithioadipate.

The thiocarboxylate silane compositions included herein may be prepared as various mixtures of individual thiocarboxylate silane components, optionally including other species as well, including wherein synthetic methods result in a distribution of various silanes and including wherein mixtures of the starting components are employed for the purpose of generating mixtures of thiocarboxylate silane products. Moreover, it is understood that the partial hydrolyzates and/or condensates of these thiocarboxylate silanes (i.e., thiocarboxylate siloxanes and/or silanols) may also be encompassed by the thiocarboxylate silanes herein, in that these partial hydrolyzates and/or condensates will be a side product of most methods of manufacture of the thiocarboxylate silanes or can occur upon storage of the thiocarboxylate silanes, especially in humid conditions, or under conditions in which residual water remaining from their preparation is not completely removed subsequent to their preparation.

Preparation of Thiocarboxylate Silane

The process herein for the preparation of thiocarboxylate-functional silane (i.e., the product) involves the reaction between aqueous thiocarboxylic acid salt (i.e., an aqueous solution containing thiocarboxylate anion) with a haloalkyl silane in the presence of a catalytically effective amount of the phase transfer catalysts described herein. Optionally, mixtures of aqueous thiocarboxylate salts and/or haloalkyl silanes can be used in which case mixtures of thiocarboxylate silanes will be obtained.

As used herein, the expression "haloalkyl silane" refers to any silane whose structure can be represented by Formula (5). Thus, "haloalkyl silane" includes silanes with one or more halogen substitutions for hydrogen on their hydrocarbon groups, as well as other substitutions which would represent potential leaving groups during nucleophilic substitution reactions, as described below. A general structure for the thiocarboxylate salt reactant is given in Formulae (IX) and (X):

$$G^1(-C(=O)S^-M^+)_e \quad (IX);$$

$$R^7C(=O)S^-M^+ \quad (X)$$

a general structure for the haloalkyl silane reactant is given in Formula (XI):

$$L_hG^2(-SiX'_3)_f \quad (XI)$$

wherein each occurrence of $R^7$ is independently selected form the group consisting of hydrogen, alkyl, cycloalkyl, alkenyl, alkynyl, aryl and aralkyl groups, with each $R^7$ other than hydrogen containing from 1 to 30 carbon atoms; each separate occurrence of $G^1$ and $G^2$ is independently a polyvalent group (divalent or higher valency) derived by substitution of an alkyl, cycloalkyl, alkenyl, aryl or aralkyl group, wherein $G^1$ and $G^2$ can contain from 1 to 30 carbon atoms; each occurrence of X' is independently a member selected from the group consisting of $R^8O—$, $R^8{}_2C=NO—$, $R^8{}_2NO—$ or $R^8{}_2N—$, $—R^8$, and $—(OSiR^8{}_2)_t(OSiR^8{}_3)$, wherein each $R^8$ is independently selected form the group consisting of hydrogen, alkyl, cycloalkyl, alkenyl, alkynyl, aryl and aralkyl groups, with each $R^8$ other than hydrogen containing from 1 to 30 carbon atoms and at least one X' is not $—R^8$ and each occurrence of the subscript t is 0 or an integer of from 1 to about 50; each occurrence of $M^+$ is each occurrence of M is an alkali metal cation, ammonium, or a mono-, di-, or tri-substituted ammonium ion where the substituents are alkyl groups of from 1 to 10 carbon atoms; and L is halogen atoms selected form the group consisting of F—, Cl—, Br— or I—; each occurrence of the subscript e is independently an integer from 2 to 6; each occurrence of the subscript f is independently an integer from 1 to 6; and, each occurrence of the subscript h is independently an integer from 1 to 6.

Representative examples of $M^+$ include sodium cation, potassium cation or trimethylammonium cation.

Representative and non-limiting haloalkyl silane reactants for use herein include 3-chloromethyl-1-triethoxysilane, 3-chloroethyl-1-triethoxysilane, 3-chloropropyl-1-triethoxysilane and 3-chlorobutyl-1-triethoxysilane. Of these, 3-chloropropyl-1-triethoxysilane is particularly advantageous.

The chemical equation (s) for reaction(s) between the aqueous thiocarboxylate salt(s) and the haloalkyl silane(s) to yield the thiocarboxylate silane(s) is (are) represented by Equations A, B, and C as follows:

$$R^7C(=O)S^-M^+ + L\text{-}G^2(\text{-SiX}'_3)_f \rightarrow RC(=O)S\text{-}G^2(\text{-SiX}'_3)_f + M^+L^- \quad (A)$$

$$G^1(\text{-}C(=O)S^-M^+)_e + eL\text{-}G^2(\text{-SiX}'_3)_f \rightarrow G^1[\text{-}C(=O)S\text{-}G^2(\text{-SiX}'_3)_f]_e + eM^+L^- \quad (B)$$

$$gG^1(\text{-}C(=O)S^-M^+)_e + dL_hG^2(\text{-SiX}'_3)_f \rightarrow [G^1(\text{-}C(=O)S—)_e]_g[G^2(\text{-SiX}'_3)_f]_d + egM^+L^- \quad (C)$$

wherein each of $R^7$, $G^1$, $G^2$, Y, L, X', and $M^+$ are as defined herein and "e", "f", "g" and "d" in Equations (A), (B) and (C) above, are the relative molar amounts of the respective reaction components.

The preparation of the product thiocarboxylate silane in accordance with the invention is carried out by combining and reacting haloalkyl silane and aqueous solution of thiocarboxylate salt in the presence of the solid inorganic-supported quaternary ammonium phase transfer catalyst described herein, usually accompanied by agitation, e.g., stirring, until the reaction has reached the desired level of completeness. Additional salt(s) may optionally be present or be added to the aqueous thiocarboxylate salt to increase the ionic strength of the solution so as to further stabilize the product silane(s) against hydrolysis. Examples of such additional salts include alkali metal salts such as the sodium and potassium halides and the corresponding carbonates and nitrates. These and similar salts can be present in the reaction medium at a level of up to about 50, and advantageously up to about 20 weight percent of the amount of thiocarboxylate salt reactant present therein.

The level of completeness of the reaction can be monitored by any means which distinguishes the reactants from the products, such as, for example, gas chromatography (GC), liquid chromatography (LC or HPLC), nuclear magnetic resonance spectroscopy (NMR), or infrared spectroscopy (IR) of the organic phase, or wet chemical analysis of the aqueous phase.

Suitable reaction conditions include temperatures of from about −30° C. to about 300° C. and pressures of ambient to about 100 atmospheres or vacuum from ambient to about 0.01 torr. Specific embodiments include conditions of from about −10° C. to about 100° C. at ambient pressure. Additional embodiments include reaction temperatures of from about 25° C. to about 100° C., and advantageously from about 40° C. to about 95° C. Variable temperatures within the aforementioned ranges may be employed, as, for example, a gradual upward or downward ramping of the temperature during the course of the reaction. In one embodiment herein the reaction period for the process of reacting the haloalkylsilane and salt of thiocarboxylate silane can be from about 5 to about 7 hours.

Ordinarily, and by way of reducing the amount of siloxane-type by-product(s) that may be formed during the thiocarboxylate silane-forming reaction, it is advantageous to conduct this reaction under continuous agitation, e.g., that provided by the motion of a conventional rotary stirrer. The vigorousness of the agitation will ordinarily be such as to keep the amount of siloxane-type by-product(s) produced during the thiocarboxylate silane-forming reaction to within reasonable bounds, e.g., less than about 20 weight percent, more commonly less than about 12 weight percent, and typically to within about 5 to about 10 weight percent, of the total amount of reaction product. The amount of agitation required to achieve this can be determined in a specific case by routine experimentation.

Suitable concentrations of the starting aqueous thiocarboxylate salt are from about 1 weight percent up to saturation, which can be as high as about 50 weight percent or more. Particular concentrations include from about 20 to about 45 weight percent and from about 30 to about 40 weight percent, with the understanding that the remaining weight percentages amounts are the amount(s) of water in the aqueous thiocarboxylate salt. Optionally, an excess of the thiocarboxylate salt relative to that demanded by the reaction stoichiometry may be used to drive the reaction to completion so as to obtain a product of minimal residual haloalkyl silane starting material, to obtain the product with minimal reaction time and/or temperature, and/or to obtain a product with minimal loss to, or contamination by, silane hydrolysis/condensation products. Alternatively, an excess of the haloalkyl silane relative to that demanded by the reaction stoichiometry may be used to reduce the residual aqueous thiocarboxylate salt content at the completion of the reaction to a minimum. In one embodiment, the amount of aqueous solution of thiocarboxylate salt can be present in the reaction medium in an amount of from about 55 weight percent to about 80 weight percent, more specifically from about 68 weight percent to about 75 weight percent. The amount of haloalkylsilane reactant can be present in the reaction medium in an amount of from about 20 weight percent to about 45 weight percent, more specifically from about 24 weight percent to about 30 weight percent.

The reaction is carried out in water. The reaction can also be carried out in water and in the presence of solvents which are insoluble or have limited solubility in water. Examples of appropriate solvents are ethers, for example, diethyl ether; hydrocarbons, for example, hexane, petroleum ether, toluene, and xylene; esters, such as ethyl acetate; and ketones, for example, di-tert-butylketone. Toluene or xylene is particularly advantageous. It is frequently advantageous to run only in water solvent.

Upon completion of the reaction, agitation is ceased resulting in the separation of the reaction mixture into two liquid phases. The organic phase (typically the upper phase) contains the thiocarboxylate silane product and the aqueous phase contains the coproduced salts plus any salts initially present or subsequently added to increase the ionic strength of the reaction medium. If a starting aqueous solution of sufficient concentration is used, a solid phase comprised of precipitated or crystallized salts may also separate. These salts may optionally be dissolved by addition of water so as to obtain a mixture made up of mainly or exclusively of two liquid phases. These phases can then be separated by decantation. The solid inorganic-supported quaternary ammonium can be separated from the reaction mixture by filtration prior to or after decantation. Any solvents used during the process may then be removed by distillation or evaporation. Residual water may be removed by vacuum and/or heat stripping. Residual particulates may subsequently or concurrently be removed by filtration. Residual haloalkyl silane may be removed by stripping under vacuum at elevated temperature.

In one embodiment, the process of making thiocarboxylate silane can be conducted in a continuous manner such that the catalyst(s) is recycled to the process, such as in one example, by filtering the solid inorganic supported-quaternary ammonium phase transfer catalyst using known means and then optionally washing the said catalyst with water and then recycling said catalyst to fresh reactants.

Alternatively, in one embodiment, the solid inorganic-supported quaternary ammonium phase transfer catalyst from the production of the aqueous thiocarboxylate salt reactant (as described below) can be also employed in the process of making the thiocarboxylate silane.

Preparation of Aqueous Thiocarboxylate Salt Reactant

If an aqueous solution of the thiocarboxylate salt(s) required for the preparation of the thiocarboxylate silane composition is not available, it may be prepared in a separate step preceding its use in the preparation of the thiocarboxylate silane composition. Alternatively, the aqueous thiocarboxylate salt may be prepared in situ and used directly thereafter, as described above, to prepare the thiocarboxylate silane composition.

If the thiocarboxylate salt is available, the aqueous solution thereof can simply be prepared by dissolving the appropriate amount of the salt into the appropriate amount of water to provide a solution of the desired concentration, or it can be prepared by dilution or evaporative concentration of whatever solution is available. Alternatively, the desired thiocarboxylate salt or aqueous solution thereof can be prepared from another salt of the desired thiocarboxylic acid. If the thiocarboxylic acid is available, the thiocarboxylate salt or aqueous solution thereof can be prepared simply by neutralizing the acid with a suitable base.

However, if neither the desired thiocarboxylic acid or one of its salts is available, it can be prepared by synthesis of the thiocarbonyl group by reaction of the appropriate acid halide and/or acid anhydride (e.g., the acid chloride) with an aqueous solution of a sulfide, a hydrosulfide, or mixture thereof (e.g., aqueous sodium hydrosulfide, NaSH), to yield an aqueous solution of the thiocarboxylate salt. If an aqueous mixture of thiocarboxylate salts is desired, the component thiocarboxylate salts can be blended, or the appropriate mixture of acid halides and/or acid anhydrides can be used in the preparation of the thiocarboxylate salts. Mixtures of one or more acid halides and acid anhydrides can optionally be used, as can mixtures of different sulfides and/or hydrosulfides when preparing either single-component or mixtures of aqueous thiocarboxylate salts.

Structures for the sulfides, hydrosulfides, and acid halides and acid anhydrides are represented by Formulae (XII), (XIII), (XIV) and (XV), respectively.

$$M^+_2S^{-2} \tag{XII}$$

$$M^+SH^- \tag{XIII}$$

$$G^1(-C(=O)-L)_e \tag{XIV}$$

$$R^7C(=O)L \tag{XV}$$

wherein each occurrence of $M^+$ is an alkali metal cation, ammonium, or a mono-, di-, or tri-substituted ammonium ion where the substituents are alkyl groups of from 1 to 10 carbon atoms; each occurrence of L is a halogen atom selected from the group consisting of F—, Cl—, Br— and I—; each separate occurrence of $G^1$ is independently $G^1$ is independently a polyvalent group (divalent or higher valency) derived by substitution of an alkyl, cycloalkyl, alkenyl, aryl or aralkyl group, wherein $G^1$ can contain from 1 to 30 carbon atoms, with the proviso that $G^1$ is not hydrogen; each occurrence of the subscript e is independently an integer from 2 to 6.

$M^+$ is typically a monocation, meaning it occurs as a cation, typically with a single positive charge. Dicationic ions could also be used in cases where their sulfides or hydrosulfides are available, suitably stable, and are sufficiently soluble in water. As such, $M^+$ is the counterion to the anionic sulfide or hydrosulfide anion. Representative examples of $M^+$ are sodium, potassium, ammonium, methyl ammonium, and triethyl ammonium. Sodium, potassium, and ammonium are especially advantageous.

The term sulfide shall refer to an alkali metal, ammonium, or substituted ammonium sulfide salt; or any mixture thereof; and The term thiocarboxylate salt, shall refer to a single-component or mixture of salts of one or more than one thiocarboxylate anion and/or counterions (cations).

Chemical equations for reactions between the aqueous sulfides and/or hydrosulfides and the acid halides and/or acid anhydrides to yield the aqueous thiocarboxylate salts are illustrated by Equations D, E, F, and G.

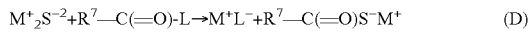  (D)

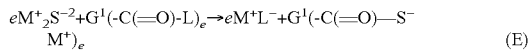  (E)

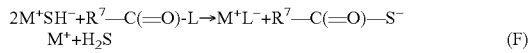  (F)

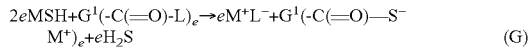  (G)

where $M^+$, $R^7$, Y, L and $G^1$ are as defined herein and "e" is defined as the relative molar amount of the respective reaction component.

The preparation of the aqueous thiocarboxylate salt is carried out by addition of the acid halide and/or acid anhydride to an aqueous solution of the sulfide and/or hydrosulfide and agitating the mixture. Due to the corrosive properties of the acid halide and/or acid anhydride, practical considerations suggest that this reaction be carried out in glass or in a glass-lined reactor.

A solid inorganic-supported quaternary ammonium phase transfer catalyst, as described herein may be added in one or several doses and/or in a continuous manner to the aqueous sulfidehydrosulfide solution, the acid halideacid anhydride, and/or the reaction mixture before, during, and/or after the addition of the acid halideacid anhydride to the aqueous sulfidehydrosulfide solution to accelerate the reaction. In an alternate embodiment, the solid inorganic-supported quaternary ammonium phase transfer catalyst used in the preparation of the aqueous thiocarboxylate salt is a homogenous catalyst (i.e., a non-solid-supported catalyst) such as the non-silica containing catalysts such as hexaethylguanidine chloride and/or tributylammonium bromide, and the like, as are well known in the art. In a further embodiment, the solid inorganic-supported quaternary ammonium phase transfer catalyst used in the preparation of the aqueous thiocarboxylate salt is a mixture of a homogenous catalyst and the phase transfer catalyst described herein for the reaction between the aqueous thiocarboxylate salt and the haloalkylsilane.

Appropriate reaction conditions for the thiocarboxylate salt-forming reaction include temperatures of from about 10° C. to about 40° C., and advantageously from about 20° C. to about 25° C., for batch operation and from about 20° C. to about 50° C., and advantageously from about 25° C. to about 40° C., for continuous operation in order to minimize or suppress by-product formation. In one embodiment the thiocarboxylate salt-forming reaction can be conducted over a period of time of from about 2 to about 3 hours.

Since the thiocarboxylate salt-forming reaction is fast and exothermic, in order the maintain the reaction within the aforesaid temperature conditions, it is advantageous to employ a reactor having temperature control capability, e.g., a jacket or coil through which a coolant such as chilled water or brine is circulated at an adjustable rate. In the absence of such temperature control capability, one can maintain the desired reaction temperature by controlling the rate of addition of the acid chloride reactant to the mixture of aqueous sulfidehydrosulfide and phase transfer catalyst.

Additional conditions of the process for making the thiocarboxylate salt include a pressure of from about 0.01 torr to about 100 atmospheres, advantageously from about 100 torr to about 2 atmospheres, and a molar ratio of sulfidehydrosulfide to acid chloride/acid anhydride of from about 2:1 to about 3:1, and advantageously from about 2:1 to about 2.2:1. The process is advantageously carried out with agitation of the reaction medium, e.g., employing a rotary stirrer, to minimize the formation of undesirable by-product(s). In general and when employing a rotary stirrer to provide agitation, the tip speed of the stirrer should be at least about 25 inches per second, advantageously at least about 30 inches per second with at least about 35 inches per second providing especially good results.

Concentrations of the starting aqueous sulfidehydrosulfide can vary from about 1 weight percent up to saturation which can be as high as about 60 weight percent or more. Specific embodiments of concentrations include from about 10 to about 40 weight percent and from about 15 to about 25 weight percent, with the understanding that the remaining weight percent is the amount of water in the aqueous sulfidehydrosulfide. In one embodiment the amount of aqueous sulfidehydrosulfide in the reaction medium is from about 56 to about 94 weight percent, more specifically from about 68 to about 84 weight percent. The amount of acid chloride/acid anhydride is from about 16 to about 31 weight percent, more specifically from about 21 to about 26 weight percent based on the total weight of the reaction medium.

The reaction is usually complete when the acid halideacid anhydride has dissolved in the aqueous phase, an exotherm is no longer evident from this reaction and the evolution of any hydrogen sulfide subsides. As previously stated, one or more additional salts may optionally be present or be added to the aqueous thiocarboxylate salt product to increase its ionic strength when used in the subsequent thiocarboxylate silane-forming reaction. At the completion of the thiocarboxylate salt-forming reaction, the solution may optionally be filtered to remove any particulate impurities and/or crystallized coproduced salts that may be present.

In one embodiment, the process of making aqueous solution of the thiocarboxylate salt(s) can be conducted in a continuous manner such that the solid inorganic supported-quaternary ammonium phase transfer catalyst(s) is recycled to the process, such as in one example, by filtering the catalyst using known means and then optionally washing the catalyst with water and then recycling the catalyst to fresh reactants.

EXAMPLES

The structure of the solid catalysts employed in the Examples is described below.

The functional group in Table 1 below refers to the N-butyl groups, the propyl spacer and the anion (halogen). The functional group loading, pore size and particle size are listed in Table 1. The spheres in the below BAP structural formulae each represent a silica particle.

The quaternary ammonium halide-functional groups account for the 5%-17% weight of the catalyst particles, while the rest is amorphous silica and hydrophobic/hydrophilic chains (see Table 1 for details). This implies that:

a) the amount of catalyst that contains 1 mmol of BAP5 functionalities can be calculated as follows: (262.6/1000)×100/15=1.75 g;

b) the amount of catalyst that contains 1 mmol of BAP7 functionalities can be calculated as follows: (307.1/1000)×100/16.4=1.87 g.

TABLE 1

Properties of solid catalysts.

|  | mw (g/mol) | Functional group loading % wt | Size particle (um) | pore (A) |
|---|---|---|---|---|
| BAP2 | 262.6 | 11.6 | 200-500 | 80-110 |
| BAP2-2 | 262.6 | 13.1 | 200-500 | 80-110 |
| BAP2-3 | 262.6 | 13.4 | 200-500 | 80-110 |
| BAP2H | 262.6 | 5-10 | 200-500 | 80-110 |
| BAP3 | 262.6 | 11.3 | 200-500 | 80-110 |
| BAP4 | 262.6 | 8.4 | 200-500 | 100-200 |
| BAP5 | 262.6 | 15.0 | 200-500 | 45-70 |
| BAP7 | 307.1 | 16.4 | 200-500 | 80-110 |
| BAP8 | 307.1 | n.a. | 60-125 | 80-110 |

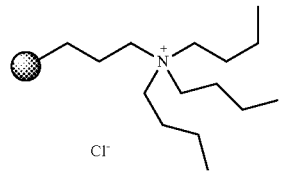

BAP2, BAP2-2, BAP2-3, BAP4 and BAP5 in Table 1 refer to: chloride, tributylammonium propyl, silica, where the number of quaternary ammonium groups is 1 or greater than 1.

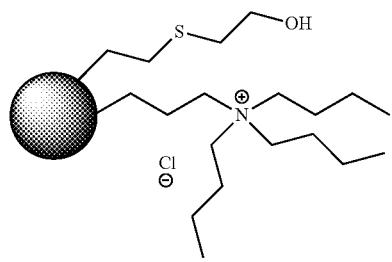

BAP2H in Table 1 refers to: chloride, tributylammonium propyl 2-hydroxyethyl silica, where the number of quaternary ammonium groups and the 2-hydroxyethyl groups bonded to silica are 1 or greater than 1.

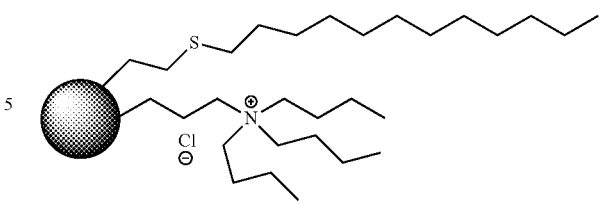

BAP3 in Table 1 refers to: chloride, tributylammonium propyl, dodecylsulfide ethyl silica, where the number of quaternary ammonium groups and the number of dodecylsulfide ethyl are 1 or greater than 1.

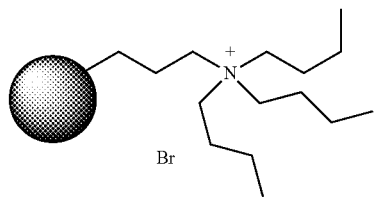

BAP7 and BAP8 in Table 1 refer to: bromide, tributylammonium propyl, silica, where the quaternary ammonium groups are 1 or greater than 1.

The homogenous catalysts employed in the examples below are:

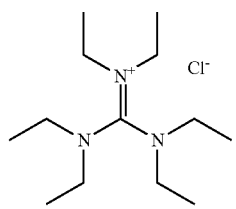 [SMILES: CCN(CC)C(N(CC)CC)=[N+](CC)CC ; [Cl-]]

Homogeneous catalyst: Hexaethylguanidinium chloride (HEG-Cl).

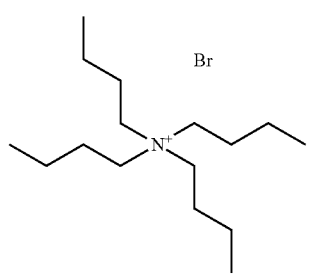 [SMILES: CCCC[N+](CCCC)(CCCC)CCCC ; Br]

Homogeneous catalyst: tetrabutylammonium bromide (TBAB).

In each of the following Examples a two-step procedure was used. The first step describes the intermediate preparation, named sodium thiooctanoate (STO) solution, while the second step deals with the 3-octanoylthio-1-propyltriethoxy silane (OTPES) synthesis reaction.

First Reaction Step: Preparation of Aqueous Sodium Thiooctanoate (STO)

In the first step the reactor, equipped with a mechanical stirrer, a condenser, a caustic scrubber and kept under an $N_2$ flow, was charged with a 24% weight NaSH aqueous solution and catalyst. The mixture was strongly stirred and octanoyl chloride (OC) was slowly added to the mixture drop wise. The reaction temperature was kept below 32° C. The STO solution preparation was completed at the end of the octanoyl chloride addition.

Second Reaction Step: Preparation of 3-Octanoylthio-1-Propyltriethoxy Silane (OTPES)

In the second step, the whole amount of STO prepared in the first stage (Examples 1 and 2) or a portion of it (Examples 3-7) was used in the OTPES synthesis process. The reactor was equipped with a mechanical stirrer, an external heating, a condenser and kept under an inert atmosphere. The STO solution was charged in the reactor, a second amount of catalyst was eventually added (see Examples for details), then the mixture was heated to the desired temperature and vigorously stirred. When the temperature was reached, 3-chloro-1-propyltriethoxysilane (CPES) was added. The mixture was then kept at the target temperature under stirring for the time necessary to get the desired composition.

The catalyst was then filtered off using a 0.2 μm filter. The two phase system was allowed to separate, then the aqueous phase was removed, while the organic phase was purified by stripping the material at 70° C. and 50 mmHg vacuum. At the end of the process, typically 40% wt of the initial mixture was organic phase and the remaining 60% was brine. The resulting product purity was typically about 82-87%.

In Examples 1-2 the solid catalyst was used both in the first and in the second step.

Example 1

First Reaction Step Conditions reaction temperature: 18<T<26° C., reaction time: 65 minutes

| Material | purity % | amount g | mol | molar ratio |
|---|---|---|---|---|
| NaSH | 24.0 | 467.8 | 2.0 | 2.2 |
| BAP7 | 16.4 | 3.4 | 0.0018 | 0.2% |
| OC | 100 | 146.6 | 0.9 | 1.0 |

Second Reaction Step Conditions reaction temperature: 95° C.; reaction time 8 hours.

| Material | purity % | amount g | mol | molar ratio |
|---|---|---|---|---|
| STO | 28.0 | 583.7 | 0.9 | 1.0 |
| CPES | 98.5 | 218.8 | 0.9 | 1.0 |
| BAP7 | 16.4 | 3.4 | 0.0018 | 0.2% |

GC results: 83.0% OTPES, 8.3% CPES, 5.2% heavies.
CPES=3-chloropropyl-1-triethoxysilane

Example 2

First Reaction Step Conditions reaction temperature: 22<T<30° C., reaction time: 50 minutes

| Material | purity % | amount g | mol | molar ratio |
|---|---|---|---|---|
| NaSH | 24.0 | 467.9 | 2.0 | 2.2 |
| BAP5 | 15.0 | 3.2 | 0.0018 | 0.2% |
| OC | 100 | 146.2 | 0.9 | 1.0 |

Second Reaction Step Conditions reaction temperature: 95° C.; reaction time: 8 hour

| Material | purity % | amount g | mol | molar ratio |
|---|---|---|---|---|
| STO | 28.0 | 583.5 | 0.9 | 1.0 |
| CPES | 98.5 | 216.4 | 0.9 | 1.0 |
| BAP5 | 15.0 | 3.4 | 0.0018 | 0.2% |

GC results: 82.7% OTPES, 8.3% CPES, 5.6% heavies.

Examples 3-4

In Example 3-4 the homogeneous catalyst was used in the first step, while a mixture of homogeneous and solid catalyst was used in the second step.

Example 3

First Reaction Step Conditions reaction temperature: 23<T<30° C., reaction time: 45 minutes

| Material | purity % | amount g | mol | molar ratio |
|---|---|---|---|---|
| NaSH | 24.0 | 468.4 | 2.0 | 2.2 |
| TBAB | 100.0 | 0.58 | 0.0018 | 0.2% |
| OC | 100.0 | 147.6 | 0.9 | 1.0 |

Second Reaction Step Conditions reaction temperature: 95° C.; reaction time: 8 hours

| Material | purity % | amount g | mol | molar ratio |
|---|---|---|---|---|
| STO | 28.0 | 117.7 | 0.18 | 1.0 |
| CPES | 98.5 | 44.6 | 0.18 | 1.0 |
| TBAB | 100.0 | 0.12 | 0.0004 | 0.2% |
| BAP7 | 16.4 | 0.68 | 0.0004 | 0.2% |

GC results: 82.1% OTPES, 5.7% CPES, 8.4% heavies.

Example 4

First Reaction Step Conditions reaction temperature: 23<T<30° C., reaction time: 45 minutes

| Material | purity % | amount g | mol | molar ratio |
|---|---|---|---|---|
| NaSH | 24.0 | 468.4 | 2.0 | 2.2 |

| Material | purity % | amount g | mol | molar ratio |
| --- | --- | --- | --- | --- |
| TBAB | 100.0 | 0.58 | 0.0018 | 0.2% |
| OC | 100.0 | 147.6 | 0.9 | 1.0 |

Second Step Conditions reaction temperature: 95° C.; reaction time: 6 hours.

| Material | purity % | amount g | mol | molar ratio |
| --- | --- | --- | --- | --- |
| STO | 28.0 | 117.7 | 0.18 | 1.0 |
| CPES | 98.5 | 44.6 | 0.18 | 1.0 |
| TBAB | 100.0 | 0.12 | 0.0004 | 0.2% |
| BAP7 | 16.4 | 0.68 | 0.0004 | 0.2% |

GC results: 85.8% OTPES, 5.8% CPES, 4.7% heavies.

Example 5

This example described scale-up conditions. The homogeneous catalyst was used in the first step, while a mixture of homogeneous and solid catalyst was used in the second step.

Example 5

First Reaction Step Conditions reaction temperature: T<32° C.; reaction time: n.a.

| Material | purity % | amount kg | kmol | molar ratio |
| --- | --- | --- | --- | --- |
| NaSH | 23.0 | 9723.8 | 39.9 | 2.2 |
| TBAB | 50.0 | 15.9 | 0.025 | 0.14% |
| OC | 100 | 2951.5 | 18.1 | 1.0 |

Second Reaction Step Conditions reaction temperature: 95° C.; reaction time: 7 hours

| Material | purity % | amount kg | kmol | molar ratio |
| --- | --- | --- | --- | --- |
| STO | 27.4 | 1441.7 | 2.17 | 1.0 |
| CPES | 98.5 | 532.9 | 2.18 | 1.0 |
| TBAB | 50.0 | 0.9 | 0.004 | 0.20% |
| BAP7 | 16.4 | 16.2 | 0.009 | 0.40% |

The process yielded 716 kg of OTPES, the rest was aqueous phase.
GC results: 87.1% OTPES, 4.2% CPES, 4.1% heavies.

Comparative Example A

First Reaction Step Conditions reaction temperature: 25<T<30° C., reaction time: 65 minutes

| Material | purity % | amount g | mol | molar ratio |
| --- | --- | --- | --- | --- |
| NaSH | 24.0 | 466.5 | 2.0 | 2.2 |
| TBAB | 100.0 | 0.59 | 0.0018 | 0.2% |
| OC | 100.0 | 147.16 | 0.9 | 1.0 |

Second Reaction Step Conditions reaction temperature: 92.5° C.; reaction time: 8 hours.

| Material | purity % | amount g | mol | molar ratio |
| --- | --- | --- | --- | --- |
| STO | 28.0 | 117.0 | 0.18 | 1.0 |
| CPES | 98.5 | 44.3 | 0.18 | 1.0 |
| TBAB | 100.0 | 0.12 | 0.0004 | 0.2% |
| HEG-Cl | 30.1 | 2.6 | 0.003 | 1.7% |

GC results: 82.0% OTPES, 5.1% CPES, 11.0% heavies.

Comparative Example B

First Reaction Step Conditions reaction temperature: 23<T<29° C., reaction time: 30 minutes.

| Material | purity % | amount g | mol | molar ratio |
| --- | --- | --- | --- | --- |
| NaSH | 24.0 | 469.2 | 2.0 | 2.2 |
| TBAB | 100.0 | 0.58 | 0.0018 | 0.2% |
| OC | 100.0 | 146.8 | 0.9 | 1.0 |

Second Reaction Step Conditions reaction temperature: 90° C.; reaction time: 7 hours

| Material | purity % | amount g | mol | molar ratio |
| --- | --- | --- | --- | --- |
| STO | 28.0 | 106.7 | 0.16 | 1.0 |
| CPES | 98.5 | 39.7 | 0.16 | 1.0 |
| TBAB | 100.0 | 0.8 | 0.0023 | 1.4% |

GC results: 85.6% OTPES, 1.0% CPES, 10.1% heavies, omega layer observed.

Example 8

The efficiency of recycled catalyst was tested: BAP3 catalyst was filtered off the end of the process and then re-used several times in the second reaction step. The STO used for this set of experiments was prepared accordingly to the $1^{st}$ step of Examples 3 and 4.

| Material | purity % | amount g | mol | molar ratio |
| --- | --- | --- | --- | --- |
| STO | 28.0 | 116.3 | 0.18 | 1.0 |
| CPES | 98.5 | 43.3 | 0.18 | 1.0 |
| TBAB | 100.0 | 0.12 | 0.0004 | 0.2% |
| BAP3 | 11.3 | 4.0 | 0.0017 | 1.0% |

Second Reaction Step Conditions reaction temperature: 90° C.; reaction time: 7 hours The catalyst was simply filtered off, washed with water and ethanol and reused again with fresh reactants.

The results are shown in the following table:

|  | BAP3 | OTPES % | CPES % | Heavies % |
|---|---|---|---|---|
| 8-A | Fresh | 78.6 | 15.0 | n.d |
| 8-B | 1$^{st}$ recycle | 77.0 | 17.2 | n.d. |
| 8-C | 2$^{nd}$ recycle | 77.8 | 16.9 | n.d. |
| 8-D | 3$^{rd}$ recycle | 75.2 | 18.8 | n.d. |

Result Summary

| Example | OTPES % | CPES % | Heavies % |
|---|---|---|---|
| 1 | 83.0 | 8.3 | 5.2 |
| 2 | 82.7 | 8.3 | 5.6 |
| 3 | 82.1 | 5.7 | 8.4 |
| 4 | 85.8 | 5.8 | 4.7 |
| 5 | 87.1 | 4.2 | 4.1 |
| Comparative Example A | 82.0 | 5.1 | 11.0 |
| Comparative Example B* | 85.6 | 1.0 | 10.1 |
| 8-A | 78.6 | 15.0 | n.d |
| 8-B | 77.0 | 17.2 | n.d. |
| 8-C | 77.8 | 16.9 | n.d. |
| 8-D | 75.2 | 18.8 | n.d. |

*a omega layer was observed at the end of the reaction
n.d. = not determined

The above noted examples clearly demonstrate the use of the solid catalyst effectively produces OTPES in quantitative amounts with much smaller levels of heavies than the exclusive use of homogenous catalyst. In addition, the solid catalyst is easily removed by simple filtration which provides for effective and quick recycling of the catalyst with effective yields.

While the invention has been described with reference to certain embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiments disclosed as the best mode contemplated for carrying out this invention but that the invention will include all embodiments falling within the scope of the appended claims.

The invention claimed is:

1. A process for the preparation of thiocarboxylate silane comprising reacting an aqueous solution of a salt of a thiocarboxylic acid with a haloalkyl silane in the presence of a solid inorganic oxide-supported phrase transfer catalyst, wherein the solid inorganic support is a metal oxide or a metalloid oxide and wherein the solid inorganic oxide-supported phase transfer catalyst comprises at least one group of the structure of formula (III):

$$[YSi(R^1)_aO_{(3-a)/2}] \quad (III)$$

wherein
each occurrence of Y is independently a quaternary ammonium halide-containing group having the structure of the formula (II):

$$[X^-][R^3R^4R^5N^+R^6{-}] \quad (II)$$

wherein each occurrence of $R^1$ is independently selected from the group consisting of an alkyl group of from 1 to 6 carbon atoms and phenyl; each $R^3$, $R^4$ and $R^5$ is independently an alkyl containing from 1 to 12 carbon atoms, phenyl or benzyl; each $R^6$ is an alkylene group containing from 1 to 6 carbon atoms;

$X^-$ is a halide selected from the group consisting of $F^-$, $Cl^-$, $Br^-$ and $I^-$; and a is an integer 0, 1 or 2, and wherein the weight percent of the $[YSi(R^1)_aO_{(3-a)/2}]$ group is from 1 to 50 weight percent, based upon the weight of the total solid support; and wherein the solid inorganic oxide-supported phase transfer catalyst formula (III) further optionally comprises an organic group having the structure of formula (IV):

$$[QSi(R^2)_bO_{(3-b)/2}] \quad (IV)$$

wherein each occurrence of $R^2$ is independently selected from the group consisting of an alkyl group of from 1 to 6 carbon atoms and phenyl; each occurrence of Q is independently an organic group selected from the group consisting of a hydrocarbon group having from 1 to 18 carbon atoms and a heterocarbon group containing from 1 to 18 carbon atoms and at least one heteroatom selected from the group consisting of oxygen, sulfur and nitrogen, with the proviso that the heterocarbon group is bonded to the silicon atom through a C—Si bond; and the subscript b is an integer 0, 1 or 2, wherein the weight percent of the $[QSi(R^2)_bO_{(3-b)/2}]$ is from 0 to 20 weight percent, where the weight percents are based upon the total weight of the solid inorganic oxide-supported quaternary ammonium halide phase transfer catalyst, to provide a thiocarboxylate silane.

2. The process of claim 1 wherein X is $Cl^-$ or $Br^-$, $R^3$, $R^4$ and $R^5$ are butyl, and $R^6$ is propyl.

3. The process of claim 1 wherein the solid inorganic oxide-supported phase transfer catalyst is a solid inorganic solid-supported quaternary ammonium halide phrase transfer catalyst which has the chemical formula (I):

$$[SiO_{4/2}]_m[YSi(R^1)_aO_{(3-a)/2}]_n[QSi(R^2)_bO_{(3-b)/2}]_o \quad (I)$$

wherein:
each occurrence of Y is independently a quaternary ammonium halide-containing group having the structure of the formula (II):

$$[X^-][R^3R^4R^5N^+R^6{-}] \quad (II)$$

wherein each $R^3$, $R^4$ and $R^5$ is independently an alkyl containing from 1 to 12 carbon atoms, phenyl or benzyl; each $R^6$ is an alkylene group containing from 1 to 6 carbon atoms; and $X^-$ is a halide selected from the group consisting of $F^-$, $Cl^-$, $Br^-$ and $I^-$;

each occurrence of Q is independently an organic group selected from the group consisting of a hydrocarbon group having from 1 to 18 carbon atoms and a heterocarbon group containing from 1 to 18 carbon atoms and at least one heteroatom selected from the group consisting of oxygen, sulfur and nitrogen, with the proviso that the heterocarbon group is bonded to the silicon atom through a C—Si bond;

each occurrence of $R^1$ and $R^2$ is independently selected from the group consisting of an alkyl group of from 1 to 6 carbon atoms and phenyl;

each occurrences of the subscripts a, b, m, n and o is independently an integer, wherein a is from 0 to 2; b is from 0 to 2; m is a positive integer, n is a positive integer and o is 0 or a positive integers, with the provisos that the molar ratio of m:n is from 5:1 to 225:1; and the molar ratio of o:n is from 0:1 to 3:1, to provide for the thiocarboxylate-containing hydrolysable silane.

4. The process of claim 2 wherein the subscripts a and b are 0, and $R^3$, $R^4$ and $R^5$ are alkyl groups, and $R^6$ is propylene.

5. The process of claim 1 wherein the solid inorganic oxide-supported phase transfer catalyst is selected from the group consisting of chloride, tributylammonium propyl, silica; chloride, tributylammonium propyl 2-hydroxyethylsulfide ethyl silica; chloride, tributylammonium propyl dodecylsulfide ethyl silica; bromide, tributylammonium propyl, silica; combinations thereof and aqueous solutions thereof.

6. The process of claim 1, wherein the salt of thiocarboxylic acid is represented by the formula: thiocarboxylate salt reactant is given in Formulae (IX) and (X):

$$G^1(\text{-}C(=O)S^-M^+)_e \quad (IX);$$

$$R^7C(=O)S^-M^+ \quad (X)$$

and the haloalkyl silane reactant is given in Formula (XI):

$$L_hG^2(\text{-}SiX'_3)_f \quad (XI)$$

wherein each occurrence of $R^7$ is independently selected form the group consisting of hydrogen, alkyl, cycloalkyl, alkenyl, alkynyl, aryl and aralkyl groups, with each $R^7$ other than hydrogen containing from 1 to 30 carbon atoms; each separate occurrence of $G^1$ and $G^2$ is independently a polyvalent group (divalent or higher valency) derived by substitution of an alkyl, cycloalkyl, alkenyl, aryl or aralkyl group, wherein $G^1$ and $G^2$ can contain from 1 to 30 carbon atoms; each occurrence of X' is independently a member selected from the group consisting of $R^8O-$, $R^8_2C=NO-$, $R^8_2NO-$ or $R^8_2N-$, $-R^8$, and $-(OSiR^8_2)_t(OSiR^8_3)$, wherein each $R^8$ is independently selected form the group consisting of hydrogen, alkyl, cycloalkyl, alkenyl, alkynyl, aryl and aralkyl groups, with each $R^8$ other than hydrogen containing from 1 to 30 carbon atoms and at least one X' is not $-R^8$ and each occurrence of the subscript t is 0 or an integer of from 1 to about 50; each occurrence of $M^+$ is each occurrence of M is an alkali metal cation, ammonium, or a mono-, di-, or tri-substituted ammonium ion where the substituents are alkyl groups of from 1 to 10 carbon atoms; and L is halogen atoms selected form the group consisting of F—, Cl—, Br— or I—; each occurrence of the subscript e is independently an integer from 2 to 6; each occurrence of the subscript f is independently an integer from 1 to 6; and, each occurrence of the subscript h is independently an integer from 1 to 6.

7. The process of claim 1, wherein the thiocarboxylate silane has the Formulae (V), (VI), (VII) and (VIII):

$$R^7C(=O)\text{---}S\text{-}G^2(\text{-}SiX'_3)_f \quad (V)$$

$$G^1[\text{-}C(=O)\text{---}S\text{-}G^2(\text{-}SiX'_3)_f]_e \quad (VI);$$

$$[G^1(\text{-}Y\text{---}S\text{---})_e]_g[G^2(\text{-}SiX'_3)_f]_d \quad (VII); \text{ and,}$$

$$X_3SiGSC(=O)GC(=O)SGSiX'_3 \quad (VIII)$$

wherein each occurrence of $R^7$ is independently selected form the group consisting of hydrogen, alkyl, cycloalkyl, alkenyl, alkynyl, aryl and aralkyl groups, with each $R^7$ other than hydrogen containing from 1 to 30 carbon atoms; each G is a divalent alkylene having from 1 to 10 carbon atoms or phenylene, each separate occurrence of $G^1$ and $G^2$ is independently a polyvalent group (divalent or higher valency) derived by substitution of an alkyl, cycloalkyl, alkenyl, aryl or aralkyl group, wherein $G^1$ and $G^2$ can contain from 1 to 30 carbon atoms; each occurrence of X' is independently a member selected from the group consisting of $R^8O-$, $R^8_2C=NO-$, $R^8_2NO-$ or $R^8_2N-$, $-R^8$, and $-(OSiR^8_2)_t(OSiR^8_3)$, wherein each $R^8$ is independently selected form the group consisting of hydrogen, alkyl, cycloalkyl, alkenyl, alkynyl, aryl and aralkyl groups, with each $R^8$ other than hydrogen containing from 1 to 30 carbon atoms and at least one X' is not $-R^8$ and each occurrence of the subscript t is 0 or an integer of from 1 to about 50; each occurrence of the subscript d is independently an integer from 1 to 100; each occurrence of the subscript e is independently an integer from 2 to 6; each occurrence of the subscript f is independently an integer from 1 to 6; and, each occurrence of the subscript g is independently an integer from 1 to 100.

8. The process of claim 3, wherein the thiocarboxyl salt has formula (X):

$$R^7C(=O)S^-M^+ \quad (X)$$

and the haloalkyl silane reactant is given in Formula (XI):

$$L_hG^2(\text{-}SiX'_3)_f \quad (XI)$$

wherein each occurrence of $R^7$ is independently selected form the group consisting of hydrogen, alkyl, cycloalkyl, alkenyl, alkynyl, aryl and aralkyl groups, with each $R^7$ other than hydrogen containing from 1 to 30 carbon atoms; each separate occurrence of $G^1$ and $G^2$ is independently a polyvalent group (divalent or higher valency) derived by substitution of an alkyl, cycloalkyl, alkenyl, aryl or aralkyl group, wherein $G^1$ and $G^2$ can contain from 1 to 30 carbon atoms; each occurrence of X' is independently a member selected from the group consisting of $R^8O-$, $R^8_2C=NO-$, $R^8_2NO-$ or $R^8_2N-$, $-R^8$, and $-(OSiR^8_2)_t(OSiR^8_3)$, wherein each $R^8$ is independently selected form the group consisting of hydrogen, alkyl, cycloalkyl, alkenyl, alkynyl, aryl and aralkyl groups, with each $R^8$ other than hydrogen containing from 1 to 30 carbon atoms and at least one X' is not $-R^8$ and each occurrence of the subscript t is 0 or an integer of from 1 to about 50; each occurrence of $M^+$ is an alkali metal cation, ammonium, or a mono-, di-, or tri-substituted ammonium ion where the substituents are alkyl groups of from 1 to 10 carbon atoms; and L is halogen atoms selected form the group consisting of F—, Cl—, Br— or I—; each occurrence of the subscript e is independently an integer from 2 to 6; each occurrence of the subscript f is independently an integer from 1 to 6; and, each occurrence of the subscript h is independently an integer equal to 1.

9. The process of claim 8 wherein $R^7$ is a primary carbon attached to the carbonyl and is advantageously a $C_2$-$C_{20}$ straight- or branched-chain alkyl, X' is ethoxide and the subscript h is 1.

10. The process of claim 1 wherein the salt of thiocarboxylic acid is present in aqueous solution up to its maximum solubility therein under the reaction conditions.

11. The process of claim 1 wherein additional salt is present during the reaction to increase the ionic strength of the reaction medium thereby increasing the stability of the product thiocarboxylate silane from hydrolysis.

12. The process of claim 11 wherein the additional salt is selected from the group consisting of alkali metal halide, alkali metal carbonate and alkali metal nitrate.

13. The process of claim 11 wherein the concentration of the salt of thiocarboxylic acid in the aqueous solution thereof is from about 20 to about 45 weight percent.

14. The process of claim 1 wherein a stoichiometric excess of salt of thiocarboxylic acid or a stoichiometric excess of haloalkyl silane is present.

15. The process of claim 1 wherein the reaction is carried out in the substantial absence of organic solvent which is insoluble in water or has limited solubility in water under the reaction conditions.

16. The process of claim 1 wherein the reaction is carried out in the presence of organic solvent which is insoluble in water or has limited solubility in water under the reaction conditions.

17. The process of claim 1 wherein the solid inorganic oxide-supported phase transfer catalyst is present in the reaction medium at a concentration of from about 1 ppm to about 15 percent by weight, based on the total weight of the reaction medium.

18. The process of claim 1 wherein the product thiocarboxylate silane is selected from the group consisting of 2-triethoxysilyl-1-ethyl thioacetate; 2-trimethoxy-silyl-1-ethyl thioacetate; 2-(methyldimethoxysilyl)-1-ethyl thioacetate; 3-trimethoxy-silyl-1-propyl thioacetate; triethoxysilylmethyl thioacetate; trimethoxysilylmethyl thioacetate; triisopropoxysilylmethyl thioacetate; methyldiethoxysilylmethyl thioacetate; methyldimethoxysilylmethyl thioacetate; methyldiisopropoxysilylmethyl thioacetate; dimethylethoxysilylmethyl thioacetate; dimethylmethoxysilylmethyl thioacetate; dimethylisopropoxysilylmethyl thioacetate; 2-triisopropoxysilyl-1-ethyl thioacetate; 2-(methyldiethoxysilyl)-1-ethyl thioacetate; 2-(methyldiisopropoxysilyl)-1-ethyl thioacetate; 2-(dimethylethoxysilyl)-1-ethyl thioacetate; 2-(dimethylmethoxy-silyl)-1-ethyl thioacetate; 2-(dimethylisopropoxysilyl)-1-ethyl thioacetate; 3-triethoxysilyl-1-propyl thioacetate; 3-triisopropoxysilyl-1-propyl thioacetate; 3-methyldiethoxysilyl-1-propyl thioacetate; 3-methyldimethoxysilyl-1-propyl thioacetate; 3-methyldiisopropoxysilyl-1-propyl thioacetate; 1-(2-triethoxysilyl-1-ethyl)-4-thioacetylcyclohexane; 1-(2-triethoxysilyl-1-ethyl)-3-thioacetylcyclohexane; 2-triethoxysilyl-5-thioacetylnorbornene; 2-triethoxysilyl-4-thioacetylnorbornene; 2-(2-triethoxysilyl-1-ethyl)-5-thioacetylnorbornene; 2-(2-triethoxysilyl-1-ethyl)-4-thioacetylnorbornene; 6-triethoxysilyl-1-hexyl thioacetate; 1-triethoxysilyl-5-hexyl thioacetate; 8-triethoxysilyl-1-octyl thioacetate; 1-triethoxysilyl-7-octyl thioacetate; 6-triethoxysilyl-1-hexyl thioacetate; 1-triethoxysilyl-5-octyl thioacetate; 8-trimethoxysilyl-1-octyl thioacetate; 1-trimethoxysilyl-7-octyl thioacetate; 10-triethoxysilyl-1-decyl thioacetate; 1-triethoxysilyl-9-decyl thioacetate; 1-triethoxysilyl-2-butyl thioacetate; 1-triethoxy-silyl-3-butyl thioacetate; 1-triethoxysilyl-3-methyl-2-butyl thioacetate; 1-triethoxysilyl-3-methyl-3-butyl thioacetate; 3-trimethoxysilyl-1-propyl thiooctanoate; 3-triethoxysilyl-1-propyl thiopalmitate; 3-triethoxysilyl-1-propyl thiooctanoate, also known as 3-octanoylthio-1-propyltriethoxy silane, 3-triethoxysilyl-1-propyl thioloctoate and 3-triethoxysilyl-1-propyl thiocaprylate; 3-triethoxysilyl-1-propyl thiodecanoate; 3-triethoxysilyl-1-propyl thiododecanoate, also known as 3-triethoxysilyl-1-propyl thiolaurate; 3-triethoxysilyl-1-propyl thiotetradecanoate, also known as 3-triethoxysilyl-1-propyl thiomyristate; 3-triethoxysilyl-1-propyl thiobenzoate; 3-triethoxysilyl-1-propyl thio-2-ethylhexanoate; 3-triethoxysilyl-1-propyl thio-2-methylheptanoate; bis-(3-triethoxysilyl-1-propyl)dithiophthalate; bis-(3-triethoxysilyl-1-propyl)dithio-iso-phthalate; bis-(3-triethoxysilyl-1-propyl)dithio-tere-phthalate; bis-(3-triethoxysilyl-1-propyl)dithiosuccinate; bis-(3-triethoxysilyl-1-propyl)dithiooxalate; bis-(3-triethoxysilyl-1-propyl)dithiosebacate; and bis-(3-triethoxysilyl-1-propyl)dithioadipate.

19. The process of claim 1 wherein the process is a continuous process which recycles the solid inorganic oxide-supported phase transfer catalyst.

20. A process for the preparation of an aqueous solution of a salt of a thiocarboxylic acid which comprises reacting an aqueous solution of a sulfide and/or hydrosulfide with an acid halide and/or acid anhydride in the presence of a solid inorganic oxide-supported phrase transfer catalyst, wherein the solid inorganic support is a metal oxide or a metalloid oxide, and wherein the and wherein the solid inorganic oxide-supported phase transfer catalyst comprises at least one group of the structure of formula (III):

$$[YSi(R^1)_aO_{(3-a)/2}] \qquad (III)$$

wherein
each occurrence of Y is independently a quaternary ammonium halide-containing group having the structure of the formula (II):

$$[X^-][R^3R^4R^5N^+R^6{-}] \qquad (II)$$

wherein each occurrence of $R^1$ is independently selected from the group consisting of an alkyl group of from 1 to 6 carbon atoms and phenyl; each $R^3$, $R^4$ and $R^5$ is independently an alkyl containing from 1 to 12 carbon atoms, phenyl or benzyl; each $R^6$ is an alkylene group containing from 1 to 6 carbon atoms;
$X^-$ is a halide selected from the group consisting of $F^-$, $Cl^-$, $Br^-$ and $I^-$; and a is an integer 0, 1 or 2, and wherein the weight percent of the $[YSi(R^1)_aO_{(3-a)/2}]$ group is from 1 to 50 weight percent, based upon the weight of the total solid support; and wherein the solid inorganic oxide-supported phase transfer catalyst formula (III) further optionally, comprises an organic group having the structure of formula (IV):

$$[QSi(R^2)_bO_{(3-b)/2}] \qquad (IV)$$

wherein each occurrence of $R^2$ is independently selected from the group consisting of an alkyl group of from 1 to 6 carbon atoms and phenyl; each occurrence of Q is independently an organic group selected from the group consisting of a hydrocarbon group having from 1 to 18 carbon atoms and a heterocarbon group containing from 1 to 18 carbon atoms and at least one heteroatom selected from the group consisting of oxygen, sulfur and nitrogen, with the proviso that the heterocarbon group is bonded to the silicon atom through a C—Si bond; and the subscript b is an integer 0, 1 or 2, wherein the weight percent of the $[QSi(R^2)_bO_{(3-b)/2}]$ is from 0 to 20 weight percent, where the weight percents are based upon the total weight of the solid inorganic oxide-supported quaternary ammonium halide phase transfer catalyst, to provide a thiocarboxylate silane.

21. The process of claim 20, wherein the structures of the sulfide and hydrosulfide are represented by the formulae:

$$M_2S$$

$$MSH$$

and the carboxylic acid halide is represented by the formulae $$R^7{-}C({=}O)S^-M^+$$

$$G^1(\text{-}C({=}O)\text{-}L)_e$$

wherein $R^7$ is independently selected form the group consisting of hydrogen, alkyl, cycloalkyl, alkenyl, alkynyl, aryl and aralkyl groups, with each $R^7$ other than hydrogen containing from 1 to 30 carbon atoms each occurrence of $M^+$ is an alkali metal cation, ammonium, or a mono-, di-, or tri-substituted ammonium ion where the substituents are alkyl groups of from 1 to 10 carbon atoms; $G^1$ is independently a polyvalent group derived by substitution of an alkyl, cycloalkyl, alkenyl, aryl or aralkyl group, wherein $G^1$ contains from 1 to 30 carbon atoms; each occurrence of L is a halogen atoms selected from the group consisting of F—, Cl—, Br— and I—; and the subscript e is 2 to 6.

22. The process of claim 20 wherein the phase transfer catalyst is selected from the group consisting of chloride, tributylammonium propyl, silica; chloride, tributylammonium propyl 2-hydroxyethyl sulfide ethyl silica; chloride, tributylammonium propyl dodecylsulfide ethyl silica; bromide, tributylammonium propyl, silica; aqueous solutions thereof; and, combinations thereof and aqueous solutions thereof.

23. The process of claim 20 wherein the process is a continuous process which recycles the catalyst.

* * * * *